US009409861B2

(12) United States Patent
Zhao et al.

(10) Patent No.: US 9,409,861 B2
(45) Date of Patent: Aug. 9, 2016

(54) MERCAPTO BENZOPHENONE COMPOUNDS, COMPOSITIONS AND PREPARATION METHOD THEREOF

(71) Applicant: Insight High Technology (Beijing) Co. Ltd., Beijing (CN)

(72) Inventors: Wenchao Zhao, Beijing (CN); Zhongli Ma, Beijing (CN); Jiaqi Li, Beijing (CN); Lixiu Yao, Beijing (CN); Jue Zhang, Beijing (CN); Weijing Hu, Beijing (CN); Jing Li, Beijing (CN); Yonglin Wang, Beijing (CN)

(73) Assignee: Insight High Technology (Beijing) Co. Ltd., Beijing (CN)

( * ) Notice: Subject to any disclaimer, the term of this patent is extended or adjusted under 35 U.S.C. 154(b) by 0 days.

(21) Appl. No.: 14/712,404

(22) Filed: May 14, 2015

(65) Prior Publication Data

US 2015/0246878 A1 Sep. 3, 2015

Related U.S. Application Data

(60) Division of application No. 13/761,751, filed on Feb. 7, 2013, now Pat. No. 9,061,979, which is a continuation of application No. PCT/CN2011/001247, filed on Jul. 29, 2011.

(51) Int. Cl.
*C07C 321/00* (2006.01)
*C07C 319/00* (2006.01)
*C07C 323/00* (2006.01)
*C07C 323/62* (2006.01)
*C07C 321/22* (2006.01)
*C07C 321/28* (2006.01)
*C07C 323/09* (2006.01)
*C08K 5/37* (2006.01)
*C07C 319/06* (2006.01)
*C07C 323/22* (2006.01)
*C07C 323/52* (2006.01)
*C08F 16/12* (2006.01)
*C08F 20/00* (2006.01)
*C08K 5/375* (2006.01)

(52) U.S. Cl.
CPC ............ *C07C 323/62* (2013.01); *C07C 319/06* (2013.01); *C07C 321/22* (2013.01); *C07C 321/28* (2013.01); *C07C 323/09* (2013.01); *C07C 323/22* (2013.01); *C07C 323/52* (2013.01); *C08F 16/12* (2013.01); *C08F 20/00* (2013.01); *C08K 5/37* (2013.01); *C08K 5/375* (2013.01)

(58) Field of Classification Search
CPC .. C07C 321/22; C07C 321/28; C07C 323/09; C07C 323/62; C07C 323/22; C07C 323/52; C07C 319/06; C08K 5/37; C08K 5/375; C08F 16/12; C08F 20/00

USPC ............................ 562/431; 568/42, 63
See application file for complete search history.

(56) References Cited

U.S. PATENT DOCUMENTS

| 3,903,322 | A | 9/1975 | Ravve et al. |
| 4,980,510 | A | 12/1990 | Hagemann et al. |
| 5,932,731 | A | 8/1999 | Goda et al. |
| 6,291,433 | B1 | 9/2001 | Barberousse et al. |
| 7,166,647 | B2 | 1/2007 | Herlihy et al. |
| 9,061,979 | B2 | 6/2015 | Zhao |
| 2004/0049972 | A1* | 3/2004 | Husemann ............... C08F 2/38 44/358 |
| 2008/0132601 | A1 | 6/2008 | Hoyle et al. |

FOREIGN PATENT DOCUMENTS

| CN | 1599713 | 3/2005 |
| CN | 101153037 | 4/2006 |
| CN | 1887913 | 1/2007 |
| CN | 101121660 | 2/2008 |
| CN | 101153037 | 4/2008 |
| CN | 101172951 | 5/2008 |
| CN | 101434534 | 5/2009 |
| CN | 101434534 A | 5/2009 |
| CN | 101434543 | 5/2009 |
| CN | 101434543 A | 5/2009 |
| CN | 101831176 A | 9/2010 |
| EP | 1 845 122 A1 | 10/2007 |

(Continued)

OTHER PUBLICATIONS

First Office Action Notice issued in CN application No. 201180011842.1, mailed Aug. 8, 2013.
Second Office Action Notice issued in CN application No. 201180011842.1, mailed Nov. 4, 2013.
Notice of Grant issued in CN application No. 201180011842, mailed Feb. 14, 2014.
Effect of New Photoinitiator on the Courses of Photochemical Reactions in Poly (Vinyl Chloride), Halina Kaczmarek et al., Polimery 2009, 54, nr. 3, pp. 202-208.
Photoinitiated Crosslinking of Multifunctional Unsaturated Cycloacetal Polythiol System, Li Miao-Zhen et al., May 1991, vol. 9, No. 2, "Photographic Science and Photochemistry," pp. 112-119 (with English abstract).

(Continued)

*Primary Examiner* — William Cheung
(74) *Attorney, Agent, or Firm* — Womble Carlyle Sandridge & Rice LLP

(57) ABSTRACT

The present invention provides a photocurable composition prepared using mercapto benzophenone compounds as key raw materials. The present invention aims to solve the problems existing in the prior photo-curing technology that low-molecular photoinitiators are easy to remain and migrate, while macromolecular photoinitiators has low initiation efficiency due to a low content of effective components and also has the problem of certain migration. The photocurable composition in the present invention can be easily prepared and has high addition efficiency with ethylenically unsaturated compounds, and the photocurable composition obtained by addition has no residual mercapto and has features of high initiation activity and zero migration rates when it is used in photocurable coatings, binder and ink formula.

7 Claims, No Drawings

(56) References Cited

FOREIGN PATENT DOCUMENTS

| WO | WO 90/01512 | 2/1990 |
|---|---|---|
| WO | WO 97/34935 | 9/1997 |
| WO | WO 2008/070737 A1 | 6/2008 |

OTHER PUBLICATIONS

Research progress on polymeric photoinitiators, Li Xiao hong et al., 1994-2010 China Academic Journal Electronic Publishing House, vol. 27, No. 6, Dec. 2007, pp. 22-26 (with English abstract).
Study of Photolysis and Photopolymerization of S-phenyl thiobenzoate, Jiang Xiao-Dong et al., China Academic Journal Electronic Publishing House © 1994-2010 ACTA Chimica Sinica 1998, pp. 979-985 (with English abstract).
Preliminary Amendment dated Mar. 6, 2013, for related parent U.S. Appl. No. 13/761,751.
Second Preliminary Amendment dated Mar. 19, 2013, for related parent U.S. Appl. No. 13/761,751.
Third Preliminary Amendment dated Mar. 26, 2013, for related parent U.S. Appl. No. 13/761,751.
Fourth Preliminary Amendment dated Mar. 12, 2014, for related parent U.S. Appl. No. 13/761,751.
Fifth Preliminary Amendment dated Mar. 18, 2014, for related parent U.S. Appl. No. 13/761,751.
Office Action dated Jul. 1, 2014, for related parent U.S. Appl. No. 13/761,751.
Amendment and Response to Restriction Requirement dated Aug. 27, 2014, for related parent U.S. Appl. No. 13/761,751.
Office Action dated Sep. 4, 2014, for related parent U.S. Appl. No. 13/761,751.
Amendment Pursuant to 37 C.F.R. § 1.111 dated Dec. 5, 2014, for related parent U.S. Appl. No. 13/761,751.
Office Action dated Jan. 9, 2015, for related parent U.S. Appl. No. 13/761,751.
Amendment Pursuant to 37 C.F.R. § 1.116 dated Mar. 5, 2015, for related parent U.S. Appl. No. 13/761,751.
Office Action dated Mar. 12, 2015, for related parent U.S. Appl. No. 13/761,751.
Amendment Pursuant to 37 C.F.R. § 1.116 dated Mar. 30, 2015, for related parent U.S. Appl. No. 13/761,751.
Notice of Allowance and Fee(s) Due dated Apr. 2, 2015, for related parent U.S. Appl. No. 13/761,751.
Part B—Fee(s) Transmittal dated May 15, 2015, for related parent U.S. Appl. No. 13/761,751.
Issue Notification dated Jun. 3, 2015, for related parent U.S. Appl. No. 13/761,751.
Extended European Search Report in EP Application No. 11870293.5 dated May 6, 2015.
Kaczmarek, H. et al., "Effect of a new photoinitiator on the courses of photochemical reactions in poly (vinyl chloride)," Polimery, vol. 54, No. 3, 2009, pp. 202-208, XP008171588, Warsaw, Poland. (Abstract).
Chinese Office Action in Chinese Application No. 2011800118421 dated Aug. 8, 2013.
Chinese Office Action in Chinese Application No. 2011800118421 dated Nov. 4, 2013.
"Photoinitiated Crosslinking of Multifunctional Unsaturated Cycloacetal Polythiol System," Photographic Science and Photochemistry, May 1991, 112-119, vol. 9, No. 2, China Academic Journal Electronic Publishing House, China. (Abstract).
F. Morlet—Savary et al., "Study of Photolysis and Photopolymerization of S-phenyl Thiobenzoate," ACTA Chimica Sinica, 1998, 979-985, China Academic Journal Electronic Publishing House, China. (Abstract).
"Research Progress on Polymeric Photoinitiators," Shanxi Chemical Industry, Dec. 2007, 22-26, vol. 27, No. 2, China Academic Journal Electronic Publishing House, China. (Abstract).

* cited by examiner

MERCAPTO BENZOPHENONE COMPOUNDS, COMPOSITIONS AND PREPARATION METHOD THEREOF

CROSS-REFERENCE TO RELATED APPLICATION

This application is a divisional application of U.S. application Ser. No. 13/761,751, filed Feb. 7, 2013, now U.S. Pat. No. 9,061,979, which is a continuation application of PCT/CN2011/001247, filed Jul. 29, 2011.

INCORPORATION BY REFERENCE

The disclosures of U.S. patent application Ser. No. 13/761,751, which was filed on Feb. 7, 2013, and PCT/CN2011/001247, which was filed on Jul. 29, 2011, are hereby incorporated by reference for all purposes as if presented herein in its entirety.

DESCRIPTION

1. Field of the Invention

The invention relates to the photo-curing technology field, particularly to a photocurable composition prepared using mercapto benzophenone compounds as raw materials, and a preparation method thereof.

2. Background of the Invention

Photo-curing technology, as a novel and advanced technology for treating material surface, has been developed rapidly since the realization of industrialization in 1960s. Particularly, its features such as high efficiency, superior quality, environmental-friendly and energy-saving enable photocurable products to be applied more and more widely. Photoinitiator is a key component of photocurable materials and plays a decisive role on the photo-curing speed of the material. When traditional low-molecular photoinitiators are used, after photocurable material coatings are cured, part of the photoinitiator absorbs light energy and decomposes into free radical which will initiate polymerization and further combine with other free radicals at the end of the polymerization, either being connected to the polymer chain, or existed in the polymerization network in the form of fragments of lower molecular weight together with residual un-decomposed photoinitiators. As time goes by, they will shift to the coating surface gradually, which will influence the appearance and performance of the coating and make the coating to become yellow, and even cause toxicity effect and influence the application on foods and sanitary packing materials. In order to overcome above-mentioned disadvantages of low-molecular photoinitiator, macromolecular photoinitiator or polymerizable photoinitiator is designed. Macromolecular photoinitiator can be connected to the chain of a macromolecule or an oligomer via carbon or oxygen atoms. At present, commercial macromolecular photoinitiator comprises KIP150 oriented KIP series and KT series products of Italy Lamberti, Speedcure series products of British Lambson and benzophenone oxygen ethanoic acid ester series containing polyether polyols as the center disclosed by Chinese Patent CN1599713; CN101434543A disclosed benzophenone oxygen ethanoic acid ester with aliphatic diol as the core; CN101172951A disclosed the preparation of hydroxyl ethoxyl benzophenone carboxylic acid ester; ZL200710090821.9 disclosed macro-molecularization of phenyl benzophenone; Chinese Patent CN1887913 disclosed the preparation of polyurethane type linked benzophenone; Polymerizable photoinitiator can incorporate polymerizable functional group such as 4-hydroxybenzophenone acrylate or metacrylic acid ester into the photoinitiator structure so as to enable the realization of marco-molecularization in the photo-curing process. This kind of products were summarized in an review named "Research Progress of Macromolecular Photoinitiator" (Shanxi Chemical Industrial Press, 2007, 27(6), 22) by Li Xiaohong.

However, macromolecular or polymerizable photoinitiators both have disadvantages of complex manufacturing process, high production cost and low product purity. For example, during the acroleic acid esterification process of 4-hydroxybenzophenone, since the initiator end and propylene end are all active groups, the esterification reaction of hydroxy is hard, and acryloyl chloride and organic amine acid binding agent must be used. Macromolecular initiators will usually have quite large molecular weights after polyether and other molecular chains are incorporated into them, and the content of effective groups is usually in an amount of only 50-60%, and compared with the corresponding low-molecular photoinitiator, the initiation activity is reduced, therefore the use dosage must be increased so as to main a proper initiation efficiency, thus the performance of the formula is reduced and the cost is increased, and customers would not like to use it, not conducive to popularization and wide application.

The photoinitiator derivatives with sulfur as bridge bond are less. U.S. Pat. No. 3,903,322 disclosed the application of 4,4'-sulfo-double benzophenone as photoinitiator in 1974, however, it can be hardly used commercially due to the high melting point of 171° C. and the low solubility; later, an improved product, i.e., 4-(4-methyl benzene sulfenyl)diphenyl ketone (BMS), had a certain application value, but the disadvantage of low solubility in acrylate monomer still existed, and the molecular weight thereof was only 304.4, so it did not have an ideal anti-mobility.

The research group of Wu Shikang in Photosensitive Chemical Research Institute Of Chinese Academy of Sciences reported a paper named "*Research on Photolysis of Sulfo-phenyl Benzoate and Photo-initiation Polymerization*" (Chemical Journal of Chinese Universities, 1998, 56, 979-85) where thiophenol was esterified with benzoic acid; in a Poland paper (Polymery, 2009, 54(3). 202-8), 4-mercapto benzophenone was esterified with p-methoxybenzoic acid, and was used for studying photo-initiation polymerization of metacrylic acid ester. This kind of photoinitiator did not become a commercial product due to some problems such as the difficulty of esterification reaction, stability of ester and dissolubility, and stink caused by various thioether compounds contained in the decomposition products.

U.S. Patent Application Publication No. US2008/0132601 disclosed a thiol photoinitiator, which fix the molecular in the polymerization network through the addition polymerization of thiol group and ethylene double bond under the action of free radical catalyst. This kind of thiol photoinitiator is prepared by substitution reaction of polythiol and chlorinated benzophenone. In fact, as the nature of raw material polythiol is similar to the nature of the product, the polythiol contained in the crude product almost cannot be separated, causing the first problem that products with good purity can be hardly obtained; the addition of polythiol compounds and ethylene double bond was studied early (Li, Miaozhen, Photographic Science and Photochemistry, 1991, 9, 112), and it has been found that the addition efficiency was unideal, and the conversion rate of thiol is only 50%, which was the second problem; in view of above-mentioned problems, this patent further proposed adding a pre-polymerization step, where thiol and acrylate were pre-polymerized in the presence of catalyst of amine compounds, forming a larger molecular weight pre-polymer containing benzophenone group, which was equal to acrylate resin commonly used in photocurable compositions, and by this way the stink of thiol molecular was removed. The third problem is that, for users of the materials, the addition of the pre-polymerization step increased operation complexity and uncertainty, and the residual amount of thiol could be hardly controlled without detecting, and the odor quality and migration rate of the cured film could not be ensured.

SUMMARY OF THE INVENTION

The purpose of the present invention is to provide a photocurable composition, a key raw material of formula (I) for preparing the photocurable composition and preparation methods thereof. The technical solution of the present invention is to solve the problems that exist in the prior photocuring technology, and the problem is that low-molecular photoinitiators are easy to remain and migrate, while macromolecular photoinitiators has a low initiation efficiency due to a low content of the effective components and also has the problem of certain migration. In the technical solution of the present invention, the key raw material of the photocurable composition can be easily prepared and has a high addition efficiency with ethylenically unsaturated compounds, and the photocurable composition obtained by addition has no residual mercapto and has features of high initiation activity and zero migration rate when it is used in photocurable coatings, binder and ink formula.

The present invention provides a photocurable composition prepared by addition reacting at least a compound of formula I with at least an ethylenically unsaturated compound capable of undergoing free radical polymerization.

Structural Formula I

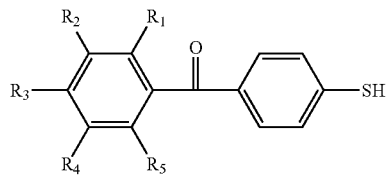

Wherein, $R_1$, $R_2$, $R_3$, $R_4$, and $R_5$ independently of one another are H, or $C_1$-$C_{12}$ alkyl, or $C_1$-$C_{12}$ alkoxy, or optionally OH and/or $OR_6$ substituted $C_2$-$C_{40}$ alkoxy, or one or more O interrupted $C_2$-$C_{40}$ alkoxy, or optionally OH and/or $OR_6$ substituted and one or more O interrupted $C_2$-$C_{40}$ alkoxy, or CN, or $CF_3$, or F, or Cl, or Br; wherein $R_6$ is $C_1$-$C_{12}$ alkyl, or phenyl; Or $R_1$, and $R_5$=H, $R_2$, $R_3$, and $R_4$ independently of one another are $SR_7$, or $NR_8R_9$, or

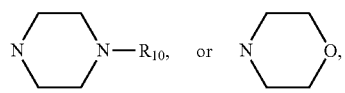

or $C_4$-$C_5$ naphthenic imino, or phenyl, or substituted phenyl, wherein $R_7$ is H, or $C_1$-$C_{12}$ alkyl, or optionally OH and/or $OR_6$ substituted $C_2$-$C_{40}$ alkyl, or one or more O interrupted $C_2$-$C_{40}$ alkyl, or optionally OH and/or $OR_6$ substituted and one or more O interrupted $C_2$-$C_{40}$ alkyl, or phenyl, or $C_1$-$C_4$ substituted phenyl, $R_8$, $R_9$, and $R_{10}$ independently of one another are $C1$-$C_{12}$ alkyl, or optionally OH and or $OR_6$ substituted $C_2$-$C_{40}$ alkyl, or one or more O interrupted $C_2$-$C_{40}$ alkyl, or optionally OH and/or $OR_6$ substituted and one or more O interrupted $C_2$-$C_{40}$ alkyl, or phenyl, or $C_1$-$C_4$ substituted phenyl, $R_6$ is $C_1$-$C_{12}$ alkyl, or phenyl; or $R_1$, $R_2$, $R_4$, and $R_5$=H, $R_3$ is $SR_7$, $NR_8R_9$,

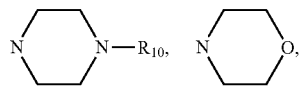

$C_4$-$C_5$ naphthenic imino, phenyl, or substituted phenyl, wherein $R_7$ is $C_1$-$C_{12}$ alkyl, or phenyl, $R_8$, $R_9$, and $R_{10}$ independently of one another are $C_1$-$C_{12}$ alkyl, optionally OH and/or $OR_6$ substituted $C_2$-$C_{40}$ alkyl, one or multiple O interrupted $C_2$-$C_{40}$ alkyl, optionally OH and/or $OR_6$ substituted and one or multiple O interrupted $C_2$-$C_{40}$ alkyl, phenyl, or $C_1$-$C_4$ substituted phenyl; wherein $R_6$ is $C_1$-$C_{12}$ alkyl, or phenyl.

In said photocurable composition, $R_1$, $R_2$, $R_3$, $R_4$, and $R_5$ in the compound of formula I can be selected from substituted groups as follows: $R_1$, $R_2$, $R_3$, $R_4$, and $R_5$ independently of one another are H, or $C_1$-$C_{12}$ alkyl, optionally OH and/or $OR_6$ substituted $C_2$-$C_{40}$ alkoxy, one or more O interrupted $C_2$-$C_{40}$ alkoxy, optionally OH and/or $OR_6$ substituted and one or more O interrupted $C_2$-$C_{40}$ alkoxy, F, Cl, or Br; wherein $R_6$ is $C_1$-$C_{12}$ alkyl, or phenyl; but $R_1$, $R_2$, $R_3$, $R_4$, and $R_5$ can not be H simultaneously; when $R_1$, $R_2$, $R_4$, and $R_5$ are H, $R_3$ is not Cl; when $R_1$, $R_3$, $R_4$, and $R_5$ are H simultaneously, $R_2$ is not Cl; when $R_1$, $R_3$, and $R_4$ are H and $R_2$ is Cl, $R_5$ is not Cl.

In above-mentioned photocurable compositions, $R_1$, $R_2$, $R_3$, $R_4$, $R_5$ in the compound of formula I can be preferably selected from substituent groups as follows: $R_2$, $R_3$, $R_4$, and $R_5$ are H, $R_1$ is methyl, or Cl, or F; or $R_1$, $R_2$, $R_4$, and $R_5$ are H, $R_3$ is methyl, or methoxy, or methylthio, or dimethylamino, or diethylamino, or F, or phenyl; or $R_1$, $R_3$, and $R_5$ are H, $R_2$ and $R_4$ independently of one another are Cl, or methyl.

In said photocurable composition, wherein said ethylenically unsaturated compound capable of undergoing free radical polymerization can include one or more unsaturated double bonds, and can be low molecular weight (monomer) or high molecular weight (oligomer). Examples of monomer including one double bond comprise alkyl-acrylate or hydroxyalkyl-acrylate, such as methyl acrylate, ethyl acrylate, butyl acrylate, acrylic acid-2-ethyl hexyl ester, 2-hydroxyethyl acrylate, isobornyl acrylate, methyl methacrylate or ethyl methacrylate. Moreover, siloxane acrylic ester, acrylonitrile, acrylamide, vinyl ether such as isobutyl vinyl ether, styrene, alkyl styrene, halogenated styrene, N-vinylpyrrolidone, vinyl chloride or vinylidene chloride can also be used.

Examples of monomer including two or more double bonds comprise ethylene glycol and polyether thereof, propylene glycol and polyether thereof, neopentyl glycol, hexanediol diacrylate or bisphenol A diacrylate, and 4,4'-di(2-propenyl acyloxy ethoxy)diphenyl propane, trimethylolpropane triacrylate, pentaerythritol triacrylate or pentaerythritol tetraacrylate, and their poly-ethoxylated or poly-propoxy derivatives, acrylic vinyl ester, divinylbenzene, succinic acid divinyl ester, diallyl phthalate, triallyl phosphate, and triallyl isocyanurate or tri(2-acrylyl ethyl) isocyanurate.

Examples of relatively high molecular weight unsaturated compounds (oligomer) comprise acrylic epoxy resin, acrylic polyester, polyester having vinyl ether or epoxy group, and polyurethane and polyether. Other examples of unsaturated oligomer comprise unsaturated polyester resin, wherein said resin is prepared with maleic acid, phthalic acid and one or more dibasic alcohols, and has a molecular weight of about 500-3000. Moreover, vinyl ether monomer or vinyl ether oligomer can be used, and oligomers capped with polyester, polyurethane, polyether, polyvinyl ether and maleic acid ester having epoxy main chain can also be used. Oligomers having vinyl ether group and mixtures of polymers disclosed in WO90/01512 are particularly applicable. Furthermore, copolymers of vinyl ether and maleic acid functionalized monomer are also applicable.

Particularly applicable examples comprise esters of double bond unsaturated carboxylic acid and polyalcohol or polyepoxide, and polymers having double bond unsaturated groups in the main chain or side chain, such as unsaturated polyester, polyamide and polyurethane and copolymer thereof, alkyd resin, polybutadiene and butadiene copolymer, polyisoprene and isoprene copolymer, and polymer and copolymer both having (methyl) acrylic group in the side chains, and mixtures of one or more of said polymers.

Examples of unsaturated carboxylic acid comprise acrylic acid, methacrylic acid, crotonic acid, itaconic acid, cinnamic acid, and unsaturated fatty acid such as linolenic acid or oleic acid, preferably acrylic acid and methacrylic acid.

The applicable polyalcohols are aromatic polyalcohols, especially ester polyalcohols and cyclic ester polyalcohols. Examples of aromatic polyalcohols comprise: hydroquinone, 4,4-dihydroxy diphenyl, 2,2-di(4-hydroxycyclohexyl phenyl) propane, and novolac and A-stage phenolic resin. Examples of polyepoxide comprise polymer and copolymer having hydroxyl groups on the chain or side chain of the polymer based on above-mentioned polyalcohols, such as polyvinyl alcohol and copolymer thereof, or methyl acrylic hydroxyl alkyl ester or copolymer thereof. Other applicable polyalcohols are oligoesters having hydroxyl end groups.

Examples of ester family polyalcohols and cyclic ester family polyalcohols comprise preferably alkylidene glycol having 2-12 carbon atoms such as ethylene glycol, 1,2- or 1,3-propylene glycol, 1,2-, 1,3- or 1,4-butylene glycol, pentylene Glycol, hexylene glycol, capryl glycol, dodecane glycol, diethylene glycol, triethylene glycol, polyethylene glycol preferably having a molecular weight of 200-1500, 1,3-cyclic pentylene glycol, 1,2-, 1,3- or 1,4-cyclic hexylene glycol, 1,4-dihydroxy methyl cyclohexane, glycerol, tri(β hydroxy ethyl) amine, trihydroxy methyl ethane, trihydroxy methyl propane, pentaerythritol, dipentaerythritol and sorbitol.

One carboxylic acid or different unsaturated carboxylic acids can be used to partly or completely esterify the polyalcohols, and in part of the obtained ester, free hydroxyl can be modified, for example etherified or esterified with other carboxylic acids.

Examples of esters comprise trimethylolpropane triacrylate, trimethylolethane triacrylate, trimethylolpropane trimethyl acrylate, trimethylolethane trimethyl acrylate, tetramethylene glycol dimethacrylate, triethylidene glycol ethylene dimethacrylate, tetraethylidene glycol diacrylate, Pentaerythritol diacrylate, Pentaerythritol triacrylate, Pentaerythritol tetraacrylate, dipentaerythritol diacrylate, 1,4-butanediol di-itaconic acid ester, sorbitol triacrylate.

Said ethylenically unsaturated compound capable of undergoing free radical polymerization also can be amides of identical or different unsaturated carboxylic acids with aromatic, cyclic ester and ester polyamines, wherein polyamine preferably have 2-6 amino groups, more preferably 2-4 amino groups. Examples of said polyamine comprise ethylenediamine, 1,2- or 1,3-propane diamine, 1,5-pentamethylene diamine, octanediamine, phenylene diamine, triethylene tetramine. Other applicable polyamines are preferably polymers and copolymers having additional amino groups in the side chains, and oligoamides having amino end groups; examples of said unsaturated amides comprise methylene dipropylene acrylamide, or diethylenetriamine trimethyl acrylamide.

Above-mentioned ethylenically unsaturated compound capable of undergoing free radical polymerization can be used alone or in any desired form of mixtures, preferably acrylate compounds, allyl ether compounds or mixture thereof.

In said photocurable composition, the compound of formula I is in an amount of 0.05-75% by weight relative to the total weight of the composition in the addition reaction.

Amine promotor compounds can be added in said photocurable composition, for example tertiary amine compounds, such as triethylamine, triethanolamine, dimethylamino ethyl benzoate, or active amine compounds, such as addition product of diethylamine and ethoxylated triMethylol propane triacrylate. The dosage of amine promotor compound is 0.05-15% by weight relative to the total weight of the composition.

Various promotors can be added in said photocurable composition in accordance with the application field and performance needed in this field, for example: pigments such as titanium dioxide or phthalo blue need to be added in color systems (colored paint, ink etc.); leveling agents need to be added in order to reach a good flow smoothness; defoaming agents need to be added in order to inhibit bubbles in a system; matting agents need to be added in order to reduce the gloss of the cured film to obtain low gloss or matte coatings, as described in *Ink Printing Manual*, 4$^{th}$ ED (compiled by Leach, R. H. etc., published by Wokingham, Van Nostrand Reinhold Press), and the additive amounts in various fields are usual doses.

Said photocurable composition can be used for various purposes, such as manufacturing photocurable printing inks, powder coatings, printing plates, binders, dental compositions, optical waveguides, color gluing systems, glass fiber cable coatings, electronic circuit board, three-dimensional objects produced via stereo-lithography and image recording materials.

The light source applicable for the present invention is an ultraviolet light (UV light) emitting apparatus, and when light with enough intensity and a spectral range of 230~450 nm is emitted onto an object coated with the photocurable composition of the present invention, polymerization can be initiated to obtain cured films, wherein the benzophenone group is connected to the polymerization network, and will not migrate and can not be extracted.

The present invention also provides a compound of formula I.

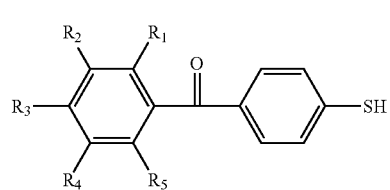

Formula I $R_1$, $R_2$, $R_3$, $R_4$, and $R_5$ independently of one another are H, $C_1$-$C_{12}$ alkyl, optionally OH and/or $OR_6$ substituted $C_2$-$C_{40}$ alkoxy, one or more O interrupted $C_2$-$C_{40}$ alkoxy, optionally OH and/or $OR_6$ substituted and one or more O interrupted $C_2$-$C_{40}$ alkoxy, F, Cl, or Br; wherein $R_6$ is $C_1$-$C_{12}$ alkyl, or phenyl; but $R_1$, $R_2$, $R_3$, $R_4$, and $R_5$ can not be H simultaneously; when $R_1$, $R_2$, $R_4$, and $R_5$ are H, $R_3$ is not Cl; when $R_1$, $R_3$, $R_4$, $R_5$ are H simultaneously, $R_2$ is not Cl; when $R_1$, $R_3$, $R_4$ are H and $R_2$ is Cl, $R_5$ is not Cl; Or $R_1$, $R_2$, $R_4$, and $R_5$=H, $R_3$ is $SR_7$, $NR_8R_9$,

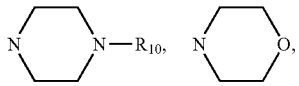

$C_4$-$C_5$ naphthenic imino, phenyl, or substituted phenyl, wherein $R_7$ is $C_1$-$C_{12}$ alkyl, or phenyl, $R_8$, $R_9$, and $R_{10}$ independently of one another are $C_1$-$C_{12}$ alkyl, optionally OH and/or $OR_6$ substituted $C_2$-$C_{40}$ alkyl, one or more O interrupted $C_2$-$C_{40}$ alkyl, optionally OH and/or $R_6$ substituted and one or more O interrupted $C_2$-$C_{40}$ alkyl, phenyl, or $C_1$-$C_4$ substituted phenyl; wherein $R_6$ is $C_1$-$C_{12}$ alkyl, or phenyl.

In the compound of formula I of the present invention, it is preferably that $R_2$, $R_3$, $R_4$, and $R_5$ are H, and $R_1$ is methyl, or Cl, or F; or $R_1$, $R_2$, $R_4$, and $R_5$ are H, and $R_3$ is methyl, methoxy, methylthio, dimethylamino, diethylamino, F, or phenyl; or $R_1$, $R_3$, and $R_5$ are H, and $R_2$ and $R_4$ each optionally is Cl, or methyl.

The present invention also provides four methods for preparing the compound of formula I, respectively being method A, method B, method C and method D, and intermediate compounds in said method A and method B. In said compound of formula I, $R_1$, $R_2$, $R_3$, $R_4$, and $R_5$ independently of one another are H, $C_1$-$C_{12}$ alkyl, $C_1$-$C_{12}$ alkoxy, optionally OH and/or $OR_6$ substituted $C_2$-$C_{40}$ alkoxy, one or more O interrupted $C_2$-$C_{40}$ alkoxy, optionally OH and/or $OR_6$ substituted and one or more O interrupted $C_2$-$C_{40}$ alkoxy, CN, $CF_3$, F, Cl, or Br; wherein $R_6$ is $C_1$-$C_{12}$ alkyl, or phenyl; Or $R_1$, and $R_5$=H, and $R_2$, $R_3$, and $R_4$ independently of one another are $SR_7$, $NR_8R_9$,

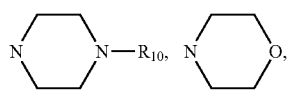

$C_4$-$C_5$ naphthenic imino, phenyl, or substituted phenyl, wherein $R_7$ is H, $C_1$-$C_{12}$ alkyl, optionally OH and/or $OR_6$ substituted $C_2$-$C_{40}$ alkyl, one or more O interrupted $C_2$-$C_{40}$ alkyl, optionally OH and/or $OR_6$ substituted and one or more O interrupted $C_2$-$C_{40}$ alkyl, phenyl, or $C_1$-$C_4$ substituted phenyl, and $R_8$, $R_9$, and $R_{10}$ each independently is $C_1$-$C_{12}$ alkyl, optionally OH and/or $OR_6$ substituted $C_2$-$C_{40}$ alkyl, one or more O interrupted $C_2$-$C_{40}$ alkyl, optionally OH and/or $R_6$ substituted and one or more O interrupted $C_2$-$C_{40}$ alkyl, or phenyl, or $C_1$-$C_4$ substituted phenyl; $R_6$ is $C_1$-$C_{12}$ alkyl, or phenyl.

Method A

Dissolving the compound of formula (II) in a solvent, feeding chlorine for chlorination reaction, and stopping the chlorination reaction when monochloride (formula III, m=1) disappears, obtaining a dichloride (formula III, m=2), a trichloride (formula III, m=3), or a mixture thereof, removing the residual chlorine and solvent at a reduced pressure, obtaining a first residue;

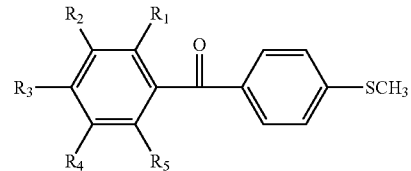

Formula II

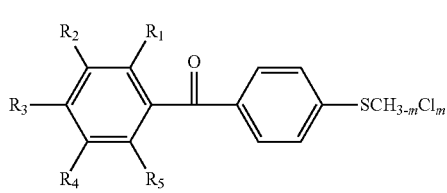

Formula III

Definitions of substituent groups $R_1$~$R_5$ in formula II and formula III are corresponding to the definitions of substituent groups $R_1$~$R_5$ in the reaction product of formula I;

(2) Adding $C_1$-$C_4$ alcohol compounds into the first residue, reacting with stirring under nitrogen protection till the chloride is consumed completely, and distilling to remove the alcohol compounds and all low-boiling-point substances, obtaining a second residue which is the compound of formula (I).

Method B (1) dissolving the compound of formula IV with X=F, Cl, Br in a strong polar organic solvent such as DMF, DME, DMSO or hexamethylphosphoramide, then adding mercaptoacetic acid or mercaptopropionic acid and solid sodium hydroxide; heating to react with stirring till the compound of formula IV disappears, obtaining a compound of formula V with y=0 or 1;

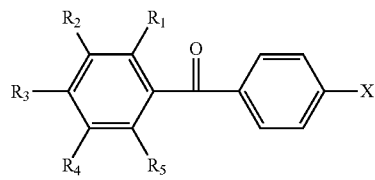

Formula IV

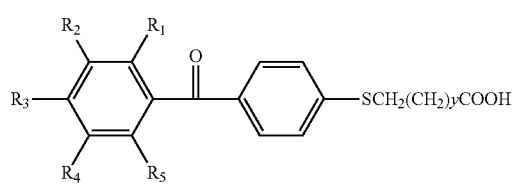

Formula V (2) dissolving the compound of formula V in a solvent, feeding chlorine for chlorination reaction, stopping the chlorination reaction when the compound of formula V disappears, removing the residual chlorine at a reduced pressure, reducing the temperature to crystallize, and filtering to obtain a mixture of chloride (formula VI, n=1) and dichloride (formula VI, n=2);

Formula VI

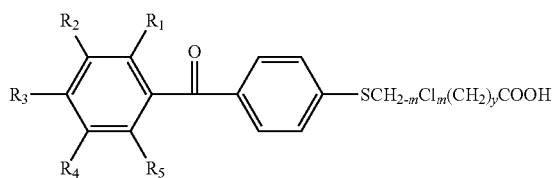

Definitions of substituent groups $R_1 \sim R_5$ in formula IV, V, and VI are corresponding to the definitions of substituent groups $R_1 \sim R_5$ in formula I;

(3) Adding $C_1$-$C_4$ alcohol compounds into the residue, reacting with stirring under nitrogen protection till the chloride is consumed completely, distilling to remove the alcohol compounds and all low-boiling-point substances, and washing with water, obtaining a residue which is the compound of formula I.

Method C (1) dissolving the compound of formula IV in a strong polar organic solvent such as DMF, DME, DMSO or hexamethylphosphoramide, adding mercaptoacetic acid and solid sodium hydroxide; heating to react with stirring till the compound of formula IV disappears, obtain a compound of formula V (y=0);

(2) Dispersing the compound of formula V (y=0) in water, and adding sulfuric acid in a catalytic amount, dropping aqueous solution of hydrogen peroxide for oxidizing till the compound of formula V disappears, cooling and separating to obtain a compound of formula VII;

Formula VII

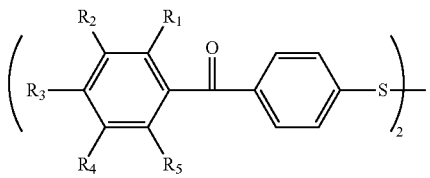

(3) dissolving the compound of formula VII in $C_1$-$C_4$ alcohol compounds, adding magnesium chips for reduction reaction till the compound of formula VII disappears, distilling to recover the excess alcohol compounds, adding hydrochloric acid for acidifying under nitrogen protection, precipitating the compound of formula I;

Definitions of substituent groups $R_1 \sim R_5$ in formula IV, V, and VII are the same as the definitions of substituent groups $R_1 \sim R_5$ in formula I;

Method D

The method is applicable to the same compound of formula I related in method A, B, and C, but except 4-mercapto benzophenone, 4'-chloro-4-mercapto benzophenone, 3'-chloro-4-mercapto benzophenone, 2',5'-dichloro-4-mercapto benzophenone, 4,4'-dimercapto benzophenone;

(1) Dissolving the compound of formula IV in a polar solvent, adding sodium sulfide or potassium sulfide, heating to react with stirring till the compound of formula IV disappears;

(2) Adding water into the reaction solution, extracting water-insoluble organic matters with water-insoluble solvent, and then acidifying the aqueous solution till the pH is less than 6, separating to obtain the precipitate which is the compound of formula I.

The photocurable composition provided in the present invention is prepared through addition reaction by mixing and contacting the compound of formula I with ethylenically unsaturated compound capable of undergoing free radical polymerization such as acrylate compounds. Firstly, in the compound of formula I, as the sulfur atom is incorporated onto the benzene ring, the ultraviolet absorption wavelength has a red shift of 65 nm relative to the maximum absorption wavelength of benzophenone, i.e., the ultraviolet absorption wavelength shifts from original 250 nm to 315 nm, enhancing the absorption efficiency of long wavelength light, and obtaining a much higher initiation rate than that of benzophenone; furthermore, thorough addition reaction can be realized by mixing the compound of formula I with ethylenically unsaturated compound capable of undergoing free radical polymerization such as ethoxylated trimethylolpropane triacrylate or Tripropylene glycol diacrylate, etc., and during the addition reaction the mercapto of the compound of formula I is added onto a double bond, so as to fix the low-molecular photoinitiator group of the compound of formula I onto compounds capable of undergoing free radical polymerization, thus forming the photocurable composition which can undergo photopolymerization reaction under photocuring conditions to obtain cured films. As prior to photocurable low-molecular photoinitiator groups have been fixed onto a polymerization monomer or a resin compound, these low-molecular photoinitiator groups will become a part of the polymerization network after polymerization, so they will not shift and migrate in the network structure and can not be extracted, therefore the curable composition of the present invention has advantages of high initiation activity and zero migration rate; meanwhile, the photocurable composition has another effect that it can distribute the initiator into places adjacent to each molecule to be polymerized in the composition to the most extent, so as to improve the double bond polymerization rate to the most extent, and thus maximally exhibit the properties of the cured film.

The preparation methods of key raw materials for preparing the photocurable composition of the present invention can be carried out easily, and the obtained product has a high purity and a high yield, suitable for industrial production. When preparing photocurable compositions according to the method provided by the present invention, monomers or resins with true self-curable properties can be produced, and coatings or ink products with properties better than products originally produced with other low-molecular photoinitiators or macromolecular photoinitiators can also be produced by the method of the present invention without changing the available production process.

EMBODIMENTS OF THE INVENTION

EXAMPLE 1

Synthesis of 4-(dichloro methyl sulfenyl)benzophenone and 4-(trichloro methyl sulfenyl)benzophenone (1) adding 4-methylthio benzophenone 30 g and dichloroethane 120 g into a 250 ml three-neck flask, and installing an vent pipe and an exhaust gas absorption device; agitating the solution to form a homogeneous solution, then cooling the solution to 0° C., and supplying chlorine slowly into the solution to undergo reaction; collecting a sample every 2 hours till 4-methylthio benzophenone disappears, analyzing to find that the reaction solution containing 4-(dichloro methyl sulfenyl)benzophenone and 4-(trichloro methyl sulfenyl)benzophenone, then stopping the reaction, and dechlorinating by nitrogen stripping, and removing dichloroethane to obtain a mixture of 4-(dichloro methyl sulfenyl)benzophenone and 4-(trichloro methyl sulfenyl)benzophenone, 41.1 g;

(2) separating by column chromatography, and crystallizing with petroleum ether to obtain a purified 4-(dichloro methyl sulfenyl)benzophenone 13.7 g, the yield 35% (white crystal), melting point 62-63° C., $^1$H-NMR data (solvent CDCl$_3$): δ6.859 ppm, s, 1H; δ7.486, 7.511, 7.536 ppm, t, 2H; δ7.603, 7.627, 7.652 ppm, t, 1H; δ7.714, 7.741 ppm, d, 2H; δ7.802, 7.82, 7.860 ppm, m, 4H), and 4-(trichloro methyl sulfenyl)benzophenone 21.8 g, the yield 50% (white crystal, melting point of 86-89° C., $^1$H-NMR data (solvent CDCl$_3$): δ7.499, 7.523, 7.548 ppm, t, 2H; δ7.618, 7.642, 7.666 ppm, t, 1H; δ7.821, 7.848 ppm, d, 2H; δ7.878~7.945 ppm, m, 4H. Wherein s represents singlet peak, d represents doublet peaks, t represents triplet peaks, q represents quartet peaks, m represents multiplet peaks, and the followings are the same.

EXAMPLE 2

Synthesis of 4-mercapto benzophenone

Method A:

(1) adding 4-methylthio benzophenone 30 g and dichloroethane 120 g in a 250 ml three-neck flask, installing an vent pipe and an exhaust gas absorption device; agitating the solution to form a homogeneous solution, then cooling it to 0° C., and supplying chlorine slowly into the solution to undergo reaction; collecting a sample every 2 hours till 4-methylthio benzophenone disappears, analyzing the reaction solution to find the existence of 4-(dichloro methyl sulfenyl)benzophenone and 4-(trichloro methyl sulfenyl)benzophenone; then continue to supply chlorine till the content of 4-(dichloro methyl sulfeny)benzophenone is less than 2%, stopping the reaction, dechlorinating by nitrogen stripping, and removing dichloroethane, obtaining a first residue which is 4-(trichloro methyl sulfenyl)benzophenone containing a few 4-(dichloro methyl sulfenyl)benzophenone; the weight of the first residue is 43.2 g, and the yield is 99%; 3 g of said first residue is crystallized in petroleum ether to obtain a purified 4-(trichloro methyl sulfenyl)benzophenone, and the purity is 98.5%.

(2) 33.2 g said first residue obtained in step (1) is added in a 100 ml three-neck flask, then adding 20 g methanol, agitating and heating the solution to reflux under nitrogen protection, after 3 hours it is analyzed to find that 4-(dichloro methyl sulfenyl)benzophenone and 4-(trichloro methyl sulfenyl) benzophenone both disappear, then distilling to remove methanal and all low-boiling-point substances, obtaining a second residue which is 4-mercapto benzophenone, with a weight of 21 g, and a yield of 98%. Said second residue is recrystallized in a mixed solvent consisting of ethyl acetate and petroleum ether in a weight ratio 1:2 to obtain 18 g white flake crystals with a purity of 99.3% and a melting point of 72-75° C., and the $^1$H-NMR data (solvent CDCl$_3$) is: δ3.657 ppm, s, 1H; δ7.315, 7.342 ppm, d, 2H; δ7.454, 7.479, 7.503 ppm, t, 2H; δ7.563, 7.587, 7.610 ppm, t, 1H; δ7.679, 7.709 ppm, d, 2H; δ7.747, 7.772 ppm, d, 2H.

Method B:

(1) Preparation of 4-(carboxymethyl sulfenyl)benzophenone 55 g 4-chloro benzophenone and 24 g mercaptoacetic acid are added into a 500 ml three-neck flask, and are dissolved with 350 ml DMF to obtain a solution, and then 23 g solid sodium hydroxide is added into the solution. Heating the solution to reflux (105-110° C.), and starting to cool the solution when the content of 4-chloro benzophenone detected by HPLC is less than 1%. The reaction solution is added into 500 ml water, and then water insoluble substances are extracted with 100 ml methylbenzene. Concentrated hydrochloric acid is used to regulate the pH value of the aqueous phase to 3-4, then some solid substances precipitates, filtering to obtain crude products, and the weight after drying is 58 g; the dried crude products are recrystallized in dichloroethane to obtain 52 g white crystal, with a yield of 75% and a melting point of 130-132° C. $^1$H-NMR data (solvent DMSO-d6): δ3.796 ppm, s, 2H; δ7.402, 7.429 ppm, d, 2H; δ7.451, 7.476, 7.501 ppm, t, 2H; δ7.567, 7.590, 7.614 ppm, t, 1H; δ7.740, 7.767 ppm, d, 2H; δ7.753, 7.775 ppm, d, 2H).

(2) 30 g said 4-(carboxymethyl sulfenyl)benzophenone (0.11 mol) is dissolved in 200 ml trichloromethane to obtain a solution. Chlorine is supplied into the solution to undergo chlorination reaction. Stopping the chlorination reaction when 4-(carboxymethyl sulfenyl)benzophenone disappear. Removing residual chlorine from the solution at a reduced pressure and concentrating the solution to being dry to obtain a mixture of 4-(carboxyl chloromethyl sulfenyl)benzophenone and 4-(carboxyl dichloromethyl sulfenyl)benzophenone (5%:95%), and the weight of said mixture is 37.5 g; 1 g said mixture is recrystallized to obtain purified 4-(carboxyl dichloromethyl sulfenyl)benzophenone, which is a white columnar crystal with a melting point of 86-87° C., $^1$H-NMR data (solvent CDCl$_3$): δ7.4931, 7.5183, 7.5437 ppm, t, 2H; δ7.6112, 7.6364, 7.6601 ppm, t, 1H; δ7.8195, 7.8449 ppm, d, 2H; δ7.8741, 7.9018, 7.9144, 7.9425 ppm, q, 4H.

(3) 34 g said mixture is added into 60 g methanol, reacting under stirring with protection of nitrogen till 4-(carboxyl chloromethyl sulfenyl)benzophenone and 4-(carboxyl dichloromethyl sulfenyl)benzophenone are consumed completely, distilling to remove methanol and all low-boiling-point substances to yield a residue, and then said residue is condensed, washed with water, and dried at a reduced pressure to yield a dry residue with a weight of 21.0 g, and the yield is 98%. Said dry residue is recrystallized in a mixed solvent consisting of ethyl acetate and petroleum ether in a weight ratio 1:2 to obtain 18 g white flake crystal of 4-mercapto benzophenone, with a purity of 99.3% and a melting point of 72-75° C.

Method C:

(1) Preparation of 4-(carboxymethyl sulfenyl)benzophenone 55 g 4-chloro benzophenone and 24 g mercaptoacetic acid are added into a 500 ml three-neck flask, and are dissolved with 350 ml DME (dimethyl acetamide) to obtain a solution, and then 23 g solid sodium hydroxide is added into the solution. Heating the solution to reflux (105-110° C.), and starting to cool the solution when the content of 4-chloro benzophenone detected by HPLC is less than 1%. The reaction solution is added into 500 ml water, and then water insoluble substances are extracted with 100 ml methylbenzene. Concentrated hydrochloric acid is used to regulate the pH value of the aqueous phase to 3-4, then some solid substances precipitate, filtering to obtain crude products, and the weight after drying is 60 g; the dried crude products are recrystallized in dichloroethane to obtain 55.3 g white crystal, and the yield was 80%.

(2) Preparation of 4,4'-diphenyl formoxyl diphenyl disulfide 20 g 4-(carboxymethyl sulfenyl)benzophenone is dispersed in 100 ml water to obtain a solution, 2 g sulfuric acid in a catalytic amount is added into the solution, then 25 g aqueous solution of hydrogen peroxide having a content of 30% is dropped into the solution under reflux to undergo oxidization reaction until 4-(carboxymethyl sulfenyl)benzophenone disappear, cooling the solution and solid substance precipitate, filtering, and then recrystallizing with 1:1 (weight ratio) ethanol/dichloroethane to obtain 12.5 g 4,4'-diphenyl formoxyl diphenyl disulfide, and the yield is 80%; the purity is 98%, a white-like powder, melting point is 124~126° C.;

(3) Reduction Reaction 10 g 4,4'-diphenyl formoxyl diphenyl disulfide is dissolved in 20 g methanol, g magnesium chips are added in batches to undergo reduction reaction. A sample is collected and analyzed until 4,4'-diphenyl formoxyl diphenyl disulfide disappear. Distilling to recover excess methanol, acidifying by adding hydrochloric acid under protection of nitrogen, and then 4-mercapto benzophenone precipitate, and the weight after drying is 10 g. Said 4-mercapto benzophenone is recrystallized in a mixed solvent consisting of ethyl acetate and petroleum ether in a weight ratio 1:2 to obtain 8.5 g white flake crystal with a purity of 99.0%, the yield is 85%, and the melting point is 72-75° C.

EXAMPLE 3

Synthesis of 4'-methyl-4-mercapto benzophenone

Method D:

(1) 120 g sodium sulfide nonahydrate is dissolved in 240 ml N, N-dimethyl formamide to obtain a solution, and 23 g 4'-methyl-4-chloro benzophenone is added into the solution. Heating the solution with stirring to react at 110° C. for 8 hours until 4'-methyl-4-chloro benzophenone disappear; the reaction solution is put into 200 ml water, hydrochloric acid having a content of 15% is used to regulate the pH value to 5-6, and then solid precipitations precipitate in the reaction solution. Filtering to obtain the precipitations, dissolving the precipitations in 100 ml methylbenzene, washing with 100 ml NaOH solution having a content of 5%, separating the solution and putting the obtained light yellow NaOH layer into a 250 ml three-neck flask; dropping diluted hydrochloric acid into the obtained light yellow NaOH aqueous solution while agitating to regulate the pH value to 5-3, then observing precipitation of off-white precipitations, filtering and separating to obtain the precipitations. The precipitations are then recrystallized in a mixed solvent consisting of ethyl acetate and petroleum ether in a weight ratio 1:5 to obtain white solid powder with a purity of 98.1%, and the weight is 9.1 g, the yield is 40%, and the melting point is 126-129° C. $^1$H-NMR data (solvent $CDCl_3$): δ2.439 ppm, s, 3H; δ3.629 ppm, s, 1H; δ7.263, 7.2908 ppm, d, 2H; δ7.311, 7.338 ppm, d, 2H; δ7.659, 7.687 ppm, s, 2H; δ7.665, 7.692 ppm, s, 2H.

EXAMPLE 4

Synthesis of 3',5'-dimethyl-4-mercapto benzophenone (1) Synthesis of 3',5'-dimethyl-4-chloro benzophenone 100 ml chlorobenzene and 14.7 g aluminium trichloride are added in a 250 ml three-neck flask, and then 16.8 g 3,5-dimethyl benzoyl chloride is dropped into the solution at room temperature. Maintaining the temperature at 70° C., react with stirring for 16 h. The reaction solution is acidolyzed and washed with water, and then is distilled to remove chlorobenzene, obtaining 21 g residue, the yield is 86%. The residue is recrystallized with ethanol to obtain a purified white crystal, and the melting point is 72-73° C. $^1$H-NMR data (solvent $CDCl_3$): δ2.371 ppm, s, 6H; δ7.230 ppm, s, 1H; δ7.363 ppm, s, 2H; δ7.438, 7.466 ppm, d, 2H; δ7.729, 7.757 ppm, d, 2H.

(2) Synthesis of 3',5'-dimethyl-4-mercapto benzophenone

Method D:

In a 250 ml three-neck flask, 10 g 3',5'-dimethyl-4-chloro benzophenone and 50 g sodium sulfide nonahydrate are dissolved in 100 ml DMF, heating the solution to react at 120° C. for 20 h. 100 ml methylbenzene is added into the reaction solution under nitrogen protection, and then diluted hydrochloric acid is added into the reaction solution to regulate the pH value to 5-6. The methylbenzene phase is separated out from the reaction solution, and 100 ml NaOH solution having a content of 5% is added. The solution is being stirred for 15 min and then is separated to obtain a light yellow aqueous solution. The pH value of the light yellow aqueous solution is adjusted to 4-5 under nitrogen protection, and solid substance precipitate in the solution. Filtering to obtain the solid precipitations, then the solid precipitations is recrystallized with ethyl acetate-petroleum ether to obtain 5.2 g light yellow flake crystal, the yield is 52%, and the melting point is 78-80° C. $^1$H-NMR data (solvent $CDCl_3$): δ2.370 ppm, s, δ6H; δ3.644 ppm, s, 1H; δ7.216 ppm, s, 1H; δ7.313, 7.340 ppm, d, 2H; δ7.352 ppm, s, 2H; δ7.668, 7.695 ppm, d, 2H.

EXAMPLE 5

Synthesis of 4'-chloro-4-mercapto benzophenone

1 Synthesis of 4'-chloro-4-methylthio benzophenone 100 ml dichloroethane and 11.81 g aluminium trichloride are added in a 250 ml three-neck flask. The solution is cooled to 0° C. 10 g thioanisole is added into the solution; maintaining the temperature at 5~-5° C., dropping 16.2 g parachlorobenzoyl chloride into the solution, and agitating the solution till thioanisole is completely reacted; the reaction solution is acidolyzed and washed with water, and dichloroethane is removed from the organic phase. Then the organic phase is recrystallized with ethanol to obtain 16.2 g white flake crystal, and the purity is 99.6%, the yield is 76.8%, and the melting point is 129~131.1° C.

2 Synthesis of 4'-chloro-4-mercapto benzophenone (1) 13.14 g 4'-chloro-4-methylthio benzophenone and 50 g dichloroethane are added into a 100 ml three-neck flask. A vent pipe and a tail gas absorption device are installed; the solution is stirred to become a homogeneous solution, and is cooled to 0° C.; chlorine is supplied slowly into the solution for reacting; after 4'-chloro-4-methylthio benzophenone disappear, chlorine is continually supplied till the content of 4'-chloro-4-(trichloromethyl sulfenyl)benzophenone is higher than 95%; distilling to remove part of the dichloroethane to obtain a residue. The residue is crystallized by cooling, and is filtered and dried to obtain 16.5 g white flake crystals; the purity of 4'-chloro-4(trichloromethyl sulfenyl) benzophenone is 98.5%, the yield is 90%, and the melting point is 116-119° C.

(2) 16.5 g said 4'-chloro-4(trichloromethyl sulfenyl)benzophenone is added in a 100 ml three-neck flask, and then 30 g methanol is added. Under nitrogen protection, the solution is heated with stirring to reflux. After reacting for 3 hours, it is analyzed to find that 4'-chloro-4(trichloromethyl sulfenyl) benzophenone is completely consumed. Distilling to remove the methanol and all low-boiling-point substances, the residue has a mass of 11.0 g, and the yield is 98%. Said residue is recrystallized in a mixed solvent consisting of dichloroethane and petroleum ether in a weight ratio 1:3 to obtain 9.5 g white flake crystal with a purity of 99.0%, and the melting point is 157-161° C. ¹H-NMR data (solvent CDCl₃): δ3.656 ppm, s, 1H; δ7.320, 7.348 ppm, d, 2H; δ7.443, 7.471 ppm, d, 2H; δ7.644, 7.672 ppm, d, 2H; δ7.698, 7.726 ppm, d, 2H.

EXAMPLE 6

Synthesis of 4'-fluorine-4-mercapto benzophenone

The preparation process is same as Example 5, except that 4-chlorobenzoyl chloride is replaced with 4-fluorine benzoyl chloride, and 4'-fluorine-4-mercapto benzophenone is obtained with a total yield of 85.2%, the appearance is white flake crystal, the melting point is 105-106° C., ¹H-NMR data (solvent CDCl₃): δ3.6535 ppm, s, 1H; δ7.1333, 7.1608, 7.1889 ppm, t, 2H; δ7.3267, 7.3533 ppm, d, 2H; δ7.6476, 7.6744 ppm, d, 2H; δ7.7849, 7.8044, 7.8115, 7.8300 ppm, q, 2H.

EXAMPLE 7

Synthesis of 2'-chloro-4-mercapto benzophenone

The preparation process is same as Example 5, except that 4-chlorobenzoyl chloride is replaced with 2-chlorobenzoyl chloride, and after completion of alcoholysis reaction, distilling to remove methanol and other low-boiling point substances to obtain a light yellow liquid, the purity of 2'-chloro-4-mercapto benzophenone is 97.8%, the yield is 80.5%, and ¹H-NMR data (solvent CDCl₃): δ3.6598 ppm, s, 1H; δ7.2831, 7.3103 ppm, d, 2H; δ7.3534~7.4471 ppm, m, 4H; δ7.6507, 7.6781 ppm, d, 2H.

EXAMPLE 8

Synthesis of 2'-fluorine-4-mercapto benzophenone

The preparation process is same as Example 5, except that 4-chlorobenzoyl chloride is replaced with 2-fluorine benzoyl chloride, and 2'-fluorine-4-mercapto benzophenone is obtained, and the yield is 83.3%, the appearance is white flake crystal, the melting point is 60-63° C., and ¹H-NMR data (solvent CDCl₃): δ3.6532 ppm, s, 1H(SH); δ7.1267, 7.1558, 7.1881 ppm, t, 1H; δ7.2399, 7.2629, 7.2859 ppm, t, 1H; δ7.2978, 7.3253 ppm, d, 2H; δ7.4929~7.5551 ppm, m, 2H; δ7.6904, 7.7168 ppm, d, 2H.

EXAMPLE 9

Synthesis of 3',5'-dichloro-4-mercapto benzophenone

1 Synthesis of 3',5'-dichloro-4-methylthio benzophenone
200 ml dichloroethane and 32 g aluminium trichloride are added into a 500 ml three-neck flask, the solution is cooled to 0° C., and 25 g thioanisole is added into the solution. A mixture of 46.1 g 3,5-dichloro benzoyl chloride and 20 ml dichloroethane is dropped into the solution while controlling the dropping temperature between 0~-5° C. The reaction solution is heated to room temperature, and is being stirred over night. Then the reaction solution is acidolyzed and washed with water, and the organic phase is concentrated, after cooling, yellow-green crystals precipitate. Filtering to obtain 50.87 g yellow-green needle-like crystals, and the purity is 98.4%, the yield is 85%, and the melting point is 108~109° C. ¹H-NMR data (solvent CDCl₃): δ2.552 ppm, s, 3H; δ7.298, 7.326 ppm, d, 2H; δ7.562 ppm, s, 1H; δ7.610 ppm, s, 2H; 7.704, 7.732 ppm, d, 2H.

2 Synthesis of 3',5'-dichloro-4-mercapto benzophenone
200 ml chlorobenzene and 30 g 3',5'-dichloro-4-methylthio benzophenone (/297.2=0.1 mol) are added into a 500 ml three-neck flask. The solution is cooled to 0° C. Chlorine is slowly supplied into the solution to undergo chlorination reaction, and the chlorination reaction is stopped till the content of 3',5'-dichloro-4-(dichloro methyl sulfenyl)benzophenone is less than 5%. Residual chlorine is removed by nitrogen stripping, and part of chlorobenzene is removed at a reduced pressure, the residue is cooled and white crystals precipitate, the weight after drying is 34.5 g, the purity of 3',5'-dichloro-4-(trichloro methyl sulfenyl)benzophenone is 98.5%, the yield is 85%, and the melting point is 114-115° C.

In a 100 ml three-neck flask, said 3',5'-dichloro-4-(trichloro methyl sulfenyl)benzophenone is added into 80 g methanol. The solution is heated with stirring under nitrogen protection to reflux for 5 h, and then is distilled to remove the methanol and all low-boiling-point substances. The residue is recrystallized in a mixed solvent consisting of ethyl acetate and petroleum ether in a weight ratio 1:1 to obtain 21 g yellow-green needle-like crystals with a purity of 98.8%, the yield is 73.5%, and the melting point is 98-99° C. ¹H-NMR data (solvent CDCl₃): δ3.6808 ppm, s, 1H; δ7.3431, 7.3700 ppm, d, 2H; δ7.5665, 7.5702 ppm, d, 1H; δ7.6033, 7.6065 ppm, d, 2H; 7.6489, 7.6758 ppm, d, 2H.

EXAMPLE 10

Synthesis of 4'-phenyl-4-mercapto benzophenone

1 Synthesis of 4'-phenyl-4-chloro benzophenone
150 g dichloroethane is added into a 500 ml reaction flask, and is cooled to 0° C., 55 g aluminium trichloride is added while agitating; dropping 64.4 g parachlorobenzoyl chloride; 54 g biphenyl is dropped and dissolved in 70 g dichloroethane solution, after 2 hours, dropping is finished, and then the temperature of the reaction solution increases to room temperature naturally; the reaction solution is stirred over night. Then the reaction solution is acidolyzed, washed with water, and distilled to remove dichloroethane at a reduced pressure. 350 ml ethanol is added into the residues for recrystallizing. Then separating and drying to obtain 87.6 g white crystals 4'-phenyl-4-chloro benzophenone, the yield is 85.3%, the melting point is 168-172° C., and the purity is 99.85%.

2 Synthesis of 4'-phenyl-4-mercapto benzophenone
15 g anhydrous potassium sulfide and 100 ml DMF are added into a 250 ml three-neck flask. The solution is heated to 50° C. under stirring, and then 8 g 4-chloro-4'-phenyl benzophenone is added into the solution; the solution is heated to reflux (about 110° C.), and is cooled after 7 h; adding 100 ml methylbenzene, regulating the pH value to 5-6 with diluted hydrochloric acid, and separating the solution; the organic phase is extracted twice with 50 ml NaOH solution having a content of 5%, and the aqueous phases are mixed; the obtained aqueous phase is put into a 250 ml three-neck flask, and nitrogen is supplied to blow for 30 min, then 15% hydrochloric acid is dropped into the aqueous solution while agitating to regulate the pH value to 5-6, and light yellow solid precipitate; filtering to obtain a light yellow solid, and the weight after drying at a reduced pressure is 5.0 g, the purity is 99.11%, the yield is 63%, the melting point is 173~176.7°C., and ¹H-NMR data (solvent CDCl3): δ3.654 ppm, s, 1H; δ7.432, 7.370 ppm, d, 2H; δ7.413, 7.436 ppm, d, 1H; δ7.466, 7.491, 7.515 ppm, t, 2H; δ7.641, 7.665 ppm, d, 2H; δ7.695, 7.719 ppm, 7.743, t, 4H; δ7.850, 7.874 ppm, d, 2H.

EXAMPLE 11

Synthesis of 4'-methylthio-4-mercapto benzophenone 15 g anhydrous potassium sulfide and 100 ml DMF are added into a 250 ml three-neck flask, agitating and heating to 50° C., then adding 10 g 4-chloro-4'-methylthio benzophenone;

heating the solution to reflux (about 110° C.), and cooling after 7 h;

adding 100 ml methylbenzene, regulating the pH value to 5-6 with 1:1 hydrochloric acid, and separating the solution; the organic phase is extracted twice with 5% NaOH solution 50 ml, and the aqueous phases are mixed together;

putting the obtained aqueous phase into a 250 ml three-neck flask, feeding nitrogen to blow for 30 min, dropping 15% hydrochloric acid while agitating to regulate the pH value to 5-6, and yellow precipitations precipitate; filtering to obtain a light yellow solid, after drying at a reduced pressure, the weight is 5.0 g, the purity is 95.5%, the yield is 50%, the melting point is 120~124° C., and $^1$H-NMR data (solvent CDCl3): δ2.544 ppm, s, 3H; δ3.641 ppm, s, 1H; δ7.277, 7.305 ppm, d, 2H; δ7.318, 7.346 ppm, d, 2H; δ7.649, 7.677 ppm, d, 2H; δ7.698, 7.726 ppm, d, 2H.

EXAMPLE 12

Synthesis of 4,4'-dimercapto benzophenone

1 Synthesis of 4,4'-dimethylthio benzophenone 15 g 4,4'-dichloro benzophenone is dissolved in 60 ml DMF, 10 g sodium methyl mercaptide is added into the solution; heating to 70° C., and after reacting with stirring for 2 h, the content of 4,4'-dichloro benzophenone detected by HPLC is less than 0.2%; the reaction solution is cooled and is added into 300 ml water, and the pH value is adjusted to 4-6, then solids precipitate, agitating for 30 min;

Leaching, and washing the filter cake with 100 ml water; the filter cake is dissolved in a mixed solvent of 105 ml ethanol and 15 ml dichloroethane to recrystallize, obtaining 13 g white crystals, the purity is 98.9%, the melting point is 123.5-123.8° C., and the yield is 79.4%.

2 Synthesis of 4,4'-di(trichloro methyl sulfenyl)benzophenone 12 g said 4,4'-dimethylthio benzophenone obtained in step 1 and 70 g chloroform are added into a 100 ml reaction flask, and are stirred to dissolve completely. Cooling to 0° C. and starting to feed chlorine till 4,4'-dimethylthio benzophenone is completely reacted; the solvent is removed at a reduced pressure to obtain 20.5 g residues. 20 g dichloroethane is added for crystallizing, obtaining 16.9 g white powder crystals, and the yield is 80.3%; the melting point is 144-146° C.

3 Synthesis of 4,4'-dimercapto benzophenone 10 g said 4,4'-di(trichloro methyl sulfenyl)benzophenone obtained in step 2, 30 g dichloroethane and 10 g ethanol are added into a 100 ml reaction flask. The solution is heated to react under reflux with nitrogen protection, and is cooled after reacting for 6 hours to precipitate solids. Filtering, and washing with ethanol to obtain 4.4 g white flake crystals, the yield is 85%, and the melting point is 179-182.3° C. $^1$H-NMR data (solvent CDCl$_3$): δ3.6369 ppm, s, 2H; δ7.3168, 7.3435 ppm, d, 4H; δ7.6384, 7.6650 ppm, d, 4H.

TABLE 1

| Compound No. | Formula | Method of preparation | Physical properties | Found C | H | S | Cl | Calculated C | H | S | Cl |
|---|---|---|---|---|---|---|---|---|---|---|---|
| 1 | benzophenone-S-CHCl$_2$ | A | 62-63° C. | 56.38 | 3.41 | 10.69 | 23.90 | 56.58 | 3.39 | 10.79 | 23.86 |
| 2 | benzophenone-S-CCl$_3$ | A | 86-89° C. | 50.60 | 2.78 | 9.60 | 32.25 | 50.70 | 2.74 | 9.67 | 32.07 |
| 3 | benzophenone-S-CCl$_2$-COOH | A | 86-87° C. | 52.69 | 3.00 | 9.31 | 20.82 | 52.80 | 2.95 | 9.40 | 20.78 |
| 4 | benzophenone-SH | A, B, C, D | 72-75° C. | 72.90 | 4.74 | 14.90 |  | 72.87 | 4.70 | 14.96 |  |

TABLE 1-continued

| Compound No. | Formula | Method of preparation | Physical properties | Analyses Found C | H | S | Cl | Calculated C | H | S | Cl |
|---|---|---|---|---|---|---|---|---|---|---|---|
| 5 | 4-CH₃-C₆H₄-CO-C₆H₄-SH | D | 126-129° C. | 73.63 | 5.35 | 14.00 | | 73.65 | 5.30 | 14.04 | |
| 6 | 3,5-(CH₃)₂-C₆H₃-CO-C₆H₄-SH | D | 78-80° C. | 74.35 | 5.86 | 13.20 | | 74.34 | 5.82 | 13.23 | |
| 7 | 4-Cl-C₆H₄-CO-C₆H₄-SH | A | 157-161° C. | 62.65 | 3.73 | 12.80 | 14.15 | 62.78 | 3.65 | 12.89 | 14.25 |
| 8 | 4-F-C₆H₄-CO-C₆H₄-SH | A | 105-106° C. | 67.15 | 3.97 | 13.72 | | 67.22 | 3.91 | 13.80 | |
| 9 | 2-Cl-C₆H₄-CO-C₆H₄-SH | A | liquid | 62.72 | 3.75 | 12.80 | 14.36 | 62.78 | 3.65 | 12.89 | 14.25 |
| 10 | 2-F-C₆H₄-CO-C₆H₄-SH | A | 60-63° C. | 67.10 | 3.96 | 13.74 | | 67.22 | 3.91 | 13.80 | |
| 11 | 3,5-Cl₂-C₆H₃-CO-C₆H₄-SH | A | 98-99° C. | 55.10 | 2.90 | 11.15 | 25.21 | 55.14 | 2.85 | 11.32 | 25.04 |
| 12 | 4-Ph-C₆H₄-CO-C₆H₄-SH | D | 173-177° C. | 78.65 | 4.88 | 11.00 | | 78.59 | 4.86 | 11.04 | |
| 13 | 4-CH₃S-C₆H₄-CO-C₆H₄-SH | D | 120-124° C. | 64.48 | 4.69 | 24.60 | | 64.58 | 4.64 | 24.63 | |

TABLE 1-continued

| Compound No. | Formula | Method of preparation | Physical properties | Analyses Found C | H | S | Cl | Calculated C | H | S | Cl |
|---|---|---|---|---|---|---|---|---|---|---|---|
| 14 | 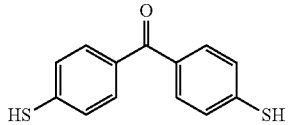 [SMILES: O=C(c1ccc(S)cc1)c1ccc(S)cc1] | A | 179-182.3° C. | 63.13 | 4.12 | 26.06 | | 63.38 | 4.09 | 26.03 | |

EXAMPLE 13

Addition of 4-mercapto benzophenone and butyl acrylate 1.07 g 4-mercapto benzophenone and 0.64 g butyl acrylate are added into a 10 ml conical flask, and are dissolved by adding 5 ml deuterated chloroform, and then are stirred for 24 h using an electromagnetic agitator, forming a colorless solution; the colorless solution is detected by nuclear magnetic resonance hydrogen spectrum, and double bond hydrogen atoms of butyl acrylate are not found, indicating that butyl acrylate is completely reacted. $^1$H-NMR data of the addition product β-(4-benzoyl thiophenyl) butyl propionate is shown in Table 2. Deuterated chloroform is removed by distilling at a reduced pressure, obtaining a residue which is a sticky liquid.

TABLE 2

| Number | Chemical Shift ppm | Peak Form | Relative Integral |
|---|---|---|---|
| 1 | 0.9108, 0.9348, 0.9589 | triplet peak | 3 |
| 2 | 1.2539~1.4424 | sextet peak | 2 |
| 3 | 1.5747~1.6683 | quintet peak | 2 |
| 4 | 2.6854, 2.7098, 2.7344 | triplet peak | 2 |
| 5 | 3.2614, 3.2858, 3.3103 | triplet peak | 2 |
| 6 | 4.0973, 4.1194, 4.1413 | triplet peak | 2 |
| 7 | 7.3543, 7.3823 | Doublet peak | 2 |
| 8 | 7.4630, 7.4862, 7.5113 | triplet peak | 2 |
| 9 | 7.5705, 7.5944, 7.6147 | triplet peak | 1 |
| 10 | 7.6818, 7.7110, 7.7399 | triplet peak | 4 |

Structure of β-(4-benzoyl thiophenyl) butyl propionate and chemical shift assignments for the hydrogen spectrum:

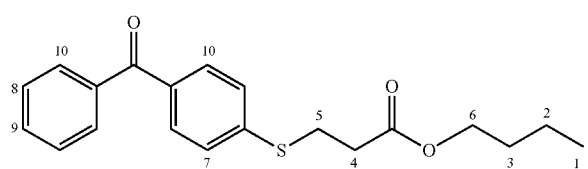 [SMILES: CCCCOC(=O)CCSc1ccc(C(=O)c2ccccc2)cc1]

EXAMPLE 14

Addition of 4-mercapto benzophenone and phenyl ethylene 1.07 g 4-mercapto benzophenone and 0.52 g phenyl ethylene are added into a 10 ml conical flask, and are dissolved by adding 2 ml deuterated chloroform, and then are stirred for 24 h using an electromagnetic agitator, forming a colorless solution; the colorless solution is detected by nuclear magnetic resonance hydrogen spectrum, finding that chemical shifts for three double bonds hydrogen atoms of the phenyl ethylene disappear, and chemical shifts for two group hydrogen atoms each having two hydrogen atoms of ethylidene appear: δ2.9798, 3.0037, 3.0308, t, 2H and δ3.2444, 3.2715, 3.2961, t, 2H, showing that double bonds of phenyl ethylene are completely added to form 4-(2-Phenethylthio)benzophenone, and the maximum absorption wavelength of UV spectrum is 315 nm.

EXAMPLE 15

Addition of 4-mercapto benzophenone and tripropylene glycol diacrylate 2.14 g 4-mercapto benzophenone (prepared by method A in Example 2) and 3.01 g tripropylene glycol diacrylate (TPGDA, Tianjin Tianjiao Chemicals Co. Ltd.) are added into a 10 ml single-neck flask, and are stirred for 24 h using an electromagnetic agitator, obtaining a colorless sticky liquid. Detecting by the high pressure liquid chromatography, 4-mercapto benzophenone is not found; the product is tripropylene Glycol [β-(4-benzoyl thiophenyl)] mixed esters with propionic acid and acrylic acid. $^1$H-NMR data (solvent CDCl$_3$): δ0.8603~1.2527 ppm, m, 9H; δ2.5801 ppm, t, 2H; δ3.3634~3.6348 ppm, m, 8H; δ4.0563~4.2183 ppm, m, 3H; δ5.8255, 5.8593 ppm, m, 1H; δ6.0698~δ6.2036 ppm, m, 1H; δ6.3709~δ6.4074 ppm, m, 1H; δ7.3569~7.7863 ppm, m, 9H.

Structure of tripropylene Glycol [β-(4-benzoyl thiophenyl)] mixed esters with propionic acid and acrylic acid:

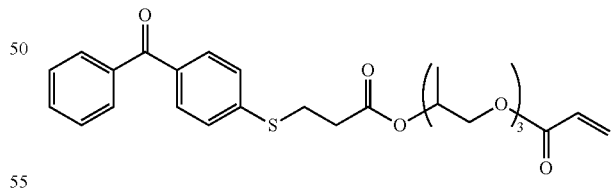

EXAMPLE 16

Equimolar Addition of 4-mercapto benzophenone and ethoxylated trimethylolpropane triacrylate 2.14 g 4-mercapto benzophenone (prepared by method A in Example 2) and 4.29 g ethoxylated trimethylolpropane triacrylate (Tianjin Tiaojiao Chemical, EO$_3$-TMPTA) are added into a 10 ml single-neck flask, and are stirred for 24 h using an electromagnetic agitator. Detected by high pressure liquid chromatography, 4-mercapto benzophenone is not found; the product is a colorless sticky liquid with a viscosity of 830 mPa·s (30° C.).

EXAMPLE 17

2:1 Addition of 4-mercapto benzophenone and ethoxylated trimethylolpropane triacrylate 4.28 g 4-mercapto benzophenone (prepared by method A in Example 2) and 4.29 g ethoxylated trimethylolpropane triacrylate (Tianjin Tiaojiao Chemical, EO$_3$-TMPTA) are added into a 10 ml single-neck flask, and are stirred for 48 h using an electromagnetic agitator. Detected by high pressure liquid chromatography, 4-mercapto benzophenone is not found; the product is a colorless sticky liquid.

EXAMPLE 18

Application of the Addition Product of 4-mercapto benzophenone and EO$_3$-TMPTA

A photocurable composition is prepared using 6.0 g addition product in Example 16 and other components according to the quantity in Table 3, and is used after standing for 48 hours.

TABLE 3

| Component | Mass (g) | Percentage (%) | Supplier |
|---|---|---|---|
| 621A-80 | 12 | 24 | Taiwan Changxing Industrial Products |
| EO$_3$-TMPTA | 30 | 60 | Tianjin Tianjiao Industrial Products |
| Active amine | 2.0 | 4 | Cytec Industrial Products P115 |
| Addition product in Example 16 | 6.0 | 12 | Experimental samples of the invention |

The prepared transparent composition is coated onto a 10×10 cm tinplate board and a 12×12 cardboard with a 15 micrometer rod applicator, and is cured with a medium voltage mercury arc lamp having a power of 80 W/cm at a speed of 20 m/min. The number of times of passing through under the lamp needed for obtaining fine surface and complete curing are recorded; the odor of the cured film on the tinplate board is evaluated manually, and the odor level is 5 in maximum and 1 in minimum. The cardboard is cut into a size of 10×10 cm, and is immersed in one simulation liquid of 100 ml distilled water or in another simulation liquid of 3% acetic acid aqueous solution, then sealed and placed for 10 days at 40° C. The printed matter is taken out, and the content of 4-mercapto benzophenone in the simulation liquid is analyzed by HPLC directly after standing. Using an EU model, assuming that 600 cm$^2$ printing area could pack 1 kg foods, the measurement results of migration ratio is expressed with ppb or µg/kg foods, the results thereof are shown in Table 7.

EXAMPLE 19

Preparing a Photocurable Composition with 4-mercapto benzophenone as Raw Materials, Measuring the Curing Speed and Migration Ratio, and Evaluating the Odor of the Film 4-mercapto benzophenone (prepared by method B in Example 2), ethoxylated trimethylolpropane triacrylate (Tianjin Tiaojiao Chemical, EO$_3$-TMPTA) and active amine are added into a 100 ml conical flask in accordance with formula ratios shown in Table 4 as below, and the solids are dissolved completely after stirred for 0.5 h using an electromagnetic agitator, then resin 621A-80 is added, continuing to stir for 2 h. Detected by high pressure liquid chromatography, 4-mercapto benzophenone is not found; the obtained photocurable composition is a colorless sticky liquid; after placing for 48 h, the obtained photocurable composition is coated and detected according to the methods in Example 18, and the data is shown in Table 7.

TABLE 4

| Component | Mass (g) | Percentage (%) | Supplier |
|---|---|---|---|
| 621A-80 | 12 | 24 | Taiwan Changxing Industrial Products |
| EO3-TMPTA | 34 | 68 | Tianjin Tianjiao Industrial Products |
| Active amine | 2.0 | 4 | Cytec Industrial Products P115 |
| 4-mercapto benzophenone | 2.0 | 4 | Samples of Example 2 in the invention |

EXAMPLE 20

Preparing a Photocurable Composition with 4'-methyl-4-mercapto benzophenone as Raw Materials The preparation process is same as Example 19, except that 4-mercapto benzophenone is replaced with 4'-methyl-4-mercapto benzophenone, and the experimental results are shown in Table 7.

EXAMPLE 21

Preparing a Photocurable Composition with 4'-chloro-4-mercapto benzophenone as Raw Materials The preparation process is same as Example 19, except that 4-mercapto benzophenone is replaced with 4'-chloro-4-mercapto benzophenone, and the experimental results are shown in Table 7.

Comparative Example 1

Preparing a Photocurable Composition with Benzophenone as Raw Materials

The preparation process is same as Example 19, except that 4-mercapto benzophenone is replaced with benzophenone, and the benzophenone exists in an adding amount in the obtained composition. The experimental results are shown in Table 7.

Comparative Example 2

Using IHT-PL 2702

The preparation process is same as Comparative Example 1, except that benzophenone is replaced with IHT-PL 2702 (products of Beijing Insight High Technology Co. Ltd.), and IHT-PL 2702 exists in an adding amount in the obtained composition. The experimental results are shown in Table 7.

EXAMPLE 22

Preparing a Photocurable Composition Containing Yellow Pigments with 4-mercapto benzophenone as Raw Materials All components are weighed in accordance with formula ratios shown in Table 5 as below. The yellow pigment color paste and the resin 621A-80 are kneaded uniformly, and then a pre-prepared composition of 4-mercapto benzophenone, $EO_3$-TMPTA and active amine are added to form a yellow photocurable composition. After placing for 48 h, the obtained yellow photocurable composition is coated and detected according to the methods in Example 18, and the data is shown in Table 7.

TABLE 5

| Component | Mass (g) | Percentage (%) | Supplier |
|---|---|---|---|
| 621A-80 | 12 | 24 | Taiwan Changxing Industrial Products |
| $EO_3$-TMPTA | 32 | 64 | Tianjin Tianjiao Industrial Products |
| Active amine | 2.0 | 4 | Cytec Industrial Products P115 |
| 4-mercapto benzophenone Kketone | 2.0 | 4 | Experimental samples of the invention |
| Yellow 3G pigment | 2.0 | 4 | BASF |

EXAMPLE 23 3',5'-dichloro-4-mercapto benzophenone was Used to Prepare a Photocurable Composition Containing Black Pigment The preparation process is same as Example 22, except that yellow pigment color paste is replaced with carbon black color paste, 4-mercapto benzophenone is replaced with 3',5'-dichloro-4-mercapto benzophenone, and the dosage ratio is according to Table 6, obtaining a black photocurable composition. After placing for 48 h, the obtained black photocurable composition is coated and detected according to the methods in Example 18, and the data is shown in Table 7.

TABLE 6

| Component | Mass (g) | Percentage (%) | Supplier |
|---|---|---|---|
| 621A-80 | 12 | 24 | Taiwan Changxing Industrial Products |
| $EO_3$-TMPTA | 32 | 64 | Tianjin Tianjiao Industrial Products |
| Active amine | 2.0 | 4 | Cytec Industrial Products P115 |
| Initiator | 2.0 | 4 | Experimental samples of the invention |
| Carbon black pigment | 2.0 | 4 | Degussa (P25) |

TABLE 7

Experimental Results of Properties Evaluation

| | | | | Migration ratio, μg/kg | |
|---|---|---|---|---|---|
| Example | Compound | Times of curing | Film odor level | water | 3% acetic acid |
| 18 | 4-mercapto benzophenone | 1 | 1 | Not Detected* | Not Detected |
| 19 | 4-mercapto benzophenone | 1 | 1 | Not Detected | Not Detected |
| 20 | 4'-methyl-4-mercapto benzophenone | 1 | 1 | Not Detected | Not Detected |
| 21 | 4'-chloro-4-mercapto benzophenone | 1 | 1 | Not Detected | Not Detected |
| Comparative 1 | Benzophenone | 2 | 5 | 1523 | 4947 |
| Comparative 2 | IHT-PL 2702 | 5 | 2 | 55 | 60 |
| 22 | 4-mercapto benzophenone | 2 | 1 | Not Detected | Not Detected |
| 23 | 3',5'-dichloro-4-mercapto benzophenone | 2 | 1 | Not Detected | Not Detected |

*limit of method detection 0.78

From the experiment results of properties evaluation in Table 7 it can be seen that, various photocurable compositions prepared with mercapto benzophenone compounds provided by the present invention as raw materials need less curing times for completely photo-curing, having a high photo-curing efficiency; the cured films have little smell; benzophenone with smaller molecular weight and macromolecule photoinitiator IHT-PL 2702 have particularly excellent performances on migration ratio and can realize zero migration.

What is claimed is:

1. An intermediate of Formula (III) for preparing a compound of Formula (I),

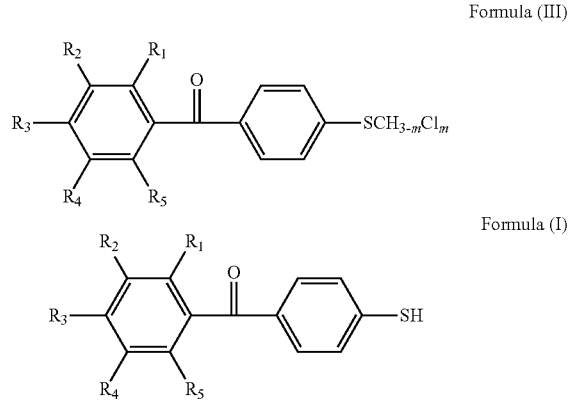

Formula (III)

Formula (I)

wherein in the compound of Formula (I), $R_1$, $R_2$, $R_3$, $R_4$, and $R_5$ independently of one another are H, $C_1$-$C_{12}$alkyl, optionally OH and/or $OR_6$ substituted $C_2$-$C_{40}$ alkoxy, one or multiple O interrupted $C_2$-$C_{40}$ alkoxy, optionally OH and/or $OR_6$ substituted and one or multiple O interrupted $C_2$-$C_{40}$ alkoxy, F, Cl, or Br and wherein $R_6$ is $C_1$-$C_{12}$ alkyl or phenyl;

with the proviso that $R_1$, $R_2$, $R_3$, $R_4$, and $R_5$ cannot be H simultaneously;

with the proviso that when $R_1$, $R_2$, $R_4$, and $R_5$ are H $R_3$ is not Cl;

with the proviso that when $R_1$, $R_3$, $R_4$, and $R_5$ are H simultaneously, $R_2$ is not Cl; when $R_1$, $R_3$, and $R_4$ are H and $R_2$ is Cl $R_5$ is not Cl; and wherein, in the intermediate Formula (III), m=1-3 and definitions of $R_1$, $R_2$, $R_3$, $R_4$, and $R_5$ are the same as definitions of $R_1$, $R_2$, $R_3$, $R_4$, and $R_5$ in the compound of Formula (I).

2. A method of preparing the compound of Formula (I) according to claim 1, comprising:
(a) reacting a mixture of chlorine, a solvent, and a compound of Formula (II) until a composition comprising a compound of Formula III is produced, wherein in the compound of Formula III, m is 2, 3, or a mixture thereof;

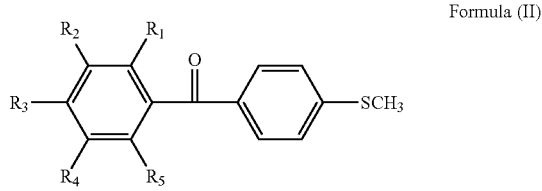
Formula (II)

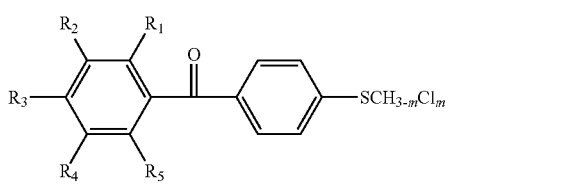
Formula (III)

wherein definitions of $R_1$, $R_2$, $R_3$, $R_4$, and $R_5$ in the compound of Formula (II) and the compound of Formula (III) are the same as the definitions of $R_1$, $R_2$, $R_3$, $R_4$, and $R_5$ of the compound of Formula (I) according to claim 1;
(b) removing solvent and unreacted chlorine from the composition comprising a compound of Formula (III) at a reduced pressure, producing a first residue thereby;
(c) reacting a $C_1$-$C_4$ alcohol with the first residue until a composition comprising the compound of Formula (I) according to claim 1 is produced; and
(d) distilling the composition comprising the compound of Formula (I) according to claim 1, producing the compound of Formula (I) thereby.

3. An intermediate of Formula (VI) for preparing the compound of Formula (I) according to claim 1,

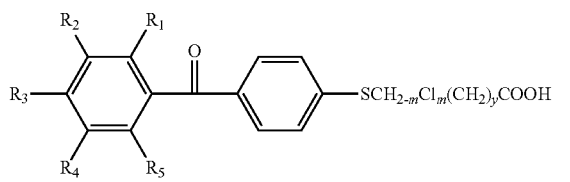
Formula (VI)

wherein m=1 or 2; y=0 or 1; and definitions of $R_1$, $R_2$, $R_3$, $R_4$, and $R_5$ are the same as definitions of $R_1$, $R_2$, $R_3$, $R_4$, and $R_5$ in the compound of Formula (I) according to claim 1.

4. A method of preparing the compound of Formula (I) according to claim 1, comprising:
(a) reacting a compound of Formula (IV) dissolved in a strong polar organic solvent with mercaptoacetic acid or mercaptopropionic acid and solid sodium hydroxide until a composition comprising a compound of Formula (V) is produced;

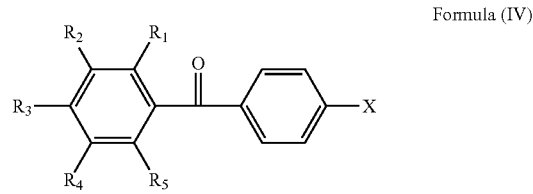
Formula (IV)

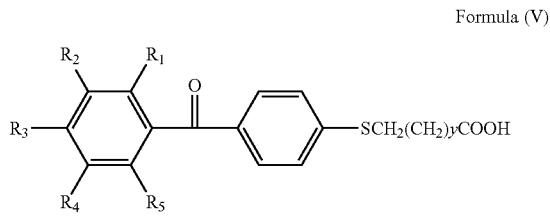
Formula (V)

wherein in the compound of Formula (IV), X is F, Cl, or Br; and
wherein in the compound of Formula (V), y is 0, 1, or a mixture thereof;
(b) reacting a mixture of chlorine, a solvent, and the composition comprising a compound of Formula (V) until a composition comprising a compound of Formula (VI) is produced,

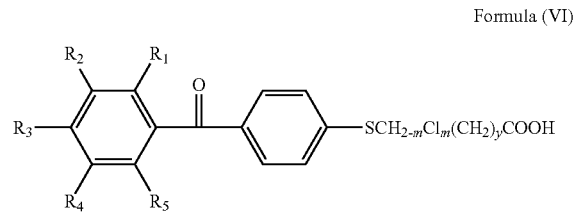
Formula (VI)

wherein in the compound of Formula (VI), m is 1, 2, or a mixture thereof; and
wherein definitions of $R_1$, R2, R3, R4, and $R_5$ in the compound of Formula (V) and the compound of Formula (VI) are the same as definitions of $R_1$, $R_2$, $R_3$, $R_4$, and $R_5$ in the compound of Formula (I) according to claim 1;
(c) removing solvent and unreacted chlorine from the composition comprising a compound of Formula (VI) at a reduced pressure, producing a first residue thereby;
(d) subjecting the first residue to a reduced temperature and subsequent filtration, producing a second residue thereby;
(e) reacting a $C_1$-$C_4$ alcohol with the second residue until a composition comprising the compound of Formula (I) according to claim 1 is produced; and
(f) distilling and subsequently washing the composition comprising the compound of Formula (I) according to claim 1, producing the compound of Formula (I) according to claim 1 thereby.

5. A method of preparing the compound of Formula (I) according to claim 1, comprising:
(a) reacting a compound of Formula (IV) dissolved in a strong polar organic solvent with mercaptoacetic acid and solid sodium hydroxide until a composition comprising a compound of Formula (V) is produced;

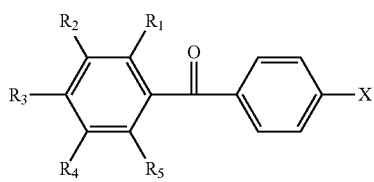

Formula (IV)

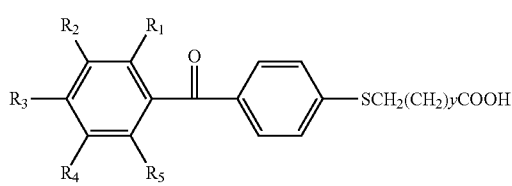

Formula (V)

wherein in the compound of Formula (IV), X is F, Cl, or Br; and wherein in the compound of Formula (V), y is 0;

(b) dispersing the composition comprising a compound of Formula (V) in water; (c) adding sulfuric acid to the composition comprising a compound of Formula (V) set forth in step (b);

(d) reacting the composition comprising a compound of Formula (V) set forth in step (c) with an aqueous solution of hydrogen peroxide under reflux conditions until a composition comprising a compound of Formula (VII) is produced;

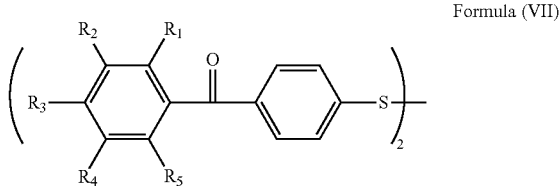

Formula (VII)

wherein definitions of $R_1$, $R_2$, $R_3$, $R_4$, and $R_5$ in the compound of Formula (V) and Formula (VII) are the same as definitions of $R_1$, $R_2$, $R_3$, $R_4$, and $R_5$ in the compound of Formula (I) according to claim 1;

(e) subjecting the composition comprising a compound of Formula (VII) to a reduced temperature and subsequent filtration, producing a first residue thereby;

(f) reacting a $C_1$-$C_4$ alcohol, and magnesium, with the first residue until a composition comprising the compound of Formula (I) according to claim 1 is produced;

(g) distilling, and subsequently acidifying the composition comprising the compound of Formula (I) according to claim 1 under nitrogen protection; and (h) precipitating the compound of Formula (I) according to claim 1 from the composition comprising the compound of Formula (I) according to claim 1.

6. A method of preparing the compound of Formula (I) according to claim 1, comprising:

(a) reacting a compound of Formula (IV) dissolved in a polar solvent, with sodium sulfide or potassium sulfide until the compound of Formula (IV) is undetectable, producing a reaction solution thereby;

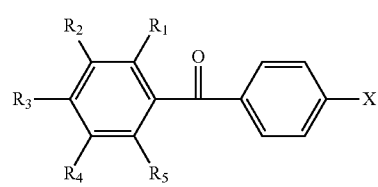

Formula (IV)

wherein in the compound of Formula (IV), X is F, Cl, or Br; and wherein definitions of $R_1$, $R_2$, $R_3$, $R_4$, and $R_5$ in the compound of Formula (IV) are the same as definitions of $R_1$, $R_2$, $R_3$, $R_4$, and $R_5$ in the compound of Formula (I) according to claim 1;

(b) adding water to the reaction solution and extracting water-insoluble organics with a water-insoluble solvent, producing an aqueous solution thereby;

(c) acidifying the aqueous solution to a pH of less than 6, producing the compound of Formula (I) thereby;

with the proviso that the compound of Formula (I) is not 4-mercapto benzophenone, 4'-chloro-4-mercapto benzophenone, 3'-chloro-4-mercapto benzophenone, 2',5'-dichloro-4-mercapto benzophenone, or 4,4'-dimercapto benzophenone.

7. The intermediate according to claim 1, wherein in the compound of Formula (I), $R_2$, $R_3$, $R_4$, and $R_5$ are H, and $R_1$ is methyl, Cl, or F; or $R_1$, $R_2$, $R_4$, and $R_5$ are H, and $R_3$ is methyl, methoxy, methylthio, dimethylamino, diethylamino, F, or phenyl; or $R_1$, $R_3$, and $R_5$ are H, and $R_2$ and $R_4$ independently of one another are Cl or methyl.

* * * * *